US009247995B2

(12) United States Patent
Suckewer (10) Patent No.: US 9,247,995 B2
(45) Date of Patent: *Feb. 2, 2016

(54) TATTOO REMOVAL WITH TWO LASER BEAMS VIA MULTI-PHOTON PROCESSES (71) Applicant: Szymon Suckewer, Princeton, NJ (US)

(72) Inventor: Szymon Suckewer, Princeton, NJ (US)

(73) Assignee: Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/532,236

(22) Filed: Nov. 4, 2014

(65) Prior Publication Data
US 2015/0057645 A1 Feb. 26, 2015

Related U.S. Application Data (63) Continuation of application No. 13/781,287, filed on Feb. 28, 2013, now Pat. No. 8,915,907, which is a continuation-in-part of application No. 13/460,442, filed on Apr. 30, 2012, now abandoned, which is a continuation of application No. 12/136,943, filed on Jun. 11, 2008, now Pat. No. 8,187,256.

(60) Provisional application No. 60/953,826, filed on Aug. 3, 2007, provisional application No. 60/944,338, filed on Jun. 15, 2007.

(51) Int. Cl.
*A61B 18/20* (2006.01)
*A61B 17/00* (2006.01)
*A61B 18/00* (2006.01)

(52) U.S. Cl.
CPC ............... *A61B 18/203* (2013.01); *A61B 18/20* (2013.01); *A61B 2017/00769* (2013.01); *A61B 2018/00452* (2013.01); *A61B 2018/00458* (2013.01); *A61B 2018/00577* (2013.01); *A61B 2018/207* (2013.01); *A61B 2018/2025* (2013.01)

(58) Field of Classification Search
USPC .................................................. 606/9; 607/88
See application file for complete search history.

(56) References Cited

U.S. PATENT DOCUMENTS

| 5,984,915 | A | * | 11/1999 | Loeb | A61B 18/203 606/15 |
| 2008/0058783 | A1 | * | 3/2008 | Altshuler | A61B 18/203 606/9 |
| 2008/0071258 | A1 | * | 3/2008 | Lemberg | A61B 18/203 606/33 |
| 2010/0082019 | A1 | * | 4/2010 | Neev | A61B 18/203 606/9 |
| 2012/0150166 | A1 | * | 6/2012 | Neev | A61B 18/203 606/33 |

* cited by examiner

*Primary Examiner* — William Thomson
*Assistant Examiner* — Jeffrey Lipitz
(74) *Attorney, Agent, or Firm* — Roy Rosser (57) ABSTRACT A method for removing tattoos using two laser beams and a multi-photon process is disclosed. A 0.1 to 100 nsec pulse secondary laser beam focused to $10^8$ W/cm$^2$ creates a temporary channel from the skin surface to the tattoo pigment. A 100 fsec pulse main laser beam is then guided through the channel to the pigment and focused to sufficient intensity, i.e., $10^{12}$ W/cm$^2$ or more, to initiate a multi-photon process that breaks up the pigment, disrupting its light reflecting properties. The channel allows the main laser beam unobstructed passage to the pigments, resulting in efficient use of the main laser. The pigment fragments escape through the temporary channel or diffuse into the blood stream. A suitably configured Ti/Sapphire laser beam is split into two components, with an uncompressed component used as the secondary laser beam, and a compressed component as the main laser beam.

7 Claims, 6 Drawing Sheets

TATTOO REMOVAL WITH TWO LASER BEAMS VIA MULTI-PHOTON PROCESSES

CLAIM OF PRIORITY

This application is a continuation of U.S. patent application Ser. No. 13/781,287 which in turn is a continuation in part of U.S. patent application Ser. No. 13/460,442 filed on Apr. 30, 2012 by Smits et al. entitled "Tattoo Removal and Other Dermatological Treatments using Multi-photon Processing" is a continuation of U.S. patent application Ser. No. 12/136,943 filed on Jun. 11, 2008 by Smits et al. titled "Tattoo Removal and other Dermatological Treatment using Multi-photon processing" that issued as U.S. Pat. No. 8,187,256 on May 29, 2012, the contents of all of which are hereby incorporated by reference.

This application is further related to, and claims priority from, U.S. Provisional Patent application No. 60/944,388 filed on Jun. 15, 2007 by Smits et al entitled "Tattoo Removal and other Dermatological Treatment using Multi-photon processing" and to U.S. Provisional Patent application No. 60/953,826 filed on Aug. 15, 2007 by Smits et al entitled "Tattoo Removal and other Dermatological Treatment using Multi-photon processing" the entire contents of both of which are hereby incorporated by reference.

FIELD OF THE INVENTION

The present invention relates to procedures and devices for dermatological treatment using multi-photon processing, and more particularly to methods and apparatus for tattoo, pigment, and blemish removal. The invention preferably includes uses 2 laser beams, one of ultra-short pulse durations, typically 50 to 100 femtoseconds (1 femtosecond=1 fsec=$1\times10^{-15}$ sec) and of very high intensity, 1012 W/cm$^2$ or greater, with a preferable intensity in the range of $10^{13}$-$10^{15}$ W/cm$^2$, for removal of pigments by multi-photon processing (the "Main Laser"), and a second laser beam (the "Secondary Laser"), of much longer pulse duration, about thousands to hundreds of thousands longer pulses, and hence with a much lower intensity, which sufficiently creates a channel in the skin for the Main Laser beam to propagate toward the pigment with minimum loss of intensity during propagation in said channel.

Although intensities of the Main Laser pulses are very high, the energy of each pulse may be low due to the short pulse duration, in the range of about 0.5 mJ to 20 mJ per pulse, although at a lower repetition rate of about 10 Hz a higher range of energy per pulse could be used, and at a higher repetition rate of 1 kHz, lower range of energy per pulse could be used.

BACKGROUND OF THE INVENTION

Tattooing is accomplished by injecting colored pigment into small holes made in the skin at various depths. The most common are "professional tattoos" with depth of holes approximately 2 to 2.5 mm and "amateur tattoos" with depth of holes approximately 1.5 mm. Tattoos may have a wide range of colors and are relatively permanent.

With the rapidly growing number of people who are acquiring tattoos, many may want to later have them removed. There is, therefore, a significant demand for the removal of tattoos. Tattoo removal, however, is not easily accomplished. In tattooing, pigments are injected into the dermis, the layer of skin that lies immediately beneath the approximately one millimeter thick epidermis, which is the dead, external surface layer of the skin. The injected pigments initially tend to aggregate in the upper dermis, close to the epidermis. One method of physically removing tattoos, therefore, requires abrading away the entire epidermis immediately above the tattoo pigment. This is a painful process, which usually leave the subject with significant scarring. Over time, the tattoo pigments may become encapsulated in fibroblasts and migrate deeper into the dermis so that older tattoos, while a little duller, are even more difficult to remove by abrasion.

With the advent of high power lasers, an alternative, non-abrading method of removing tattoos, which relies on thermal photoablation, became possible. In this method, the laser wavelength is chosen so that the tattoo pigment absorbs the laser light more readily than the surrounding skin. The laser pulses are then made powerful enough so that the pigment heats up sufficiently to thermally photoablate, i.e., dissociate, into small fragments. These fragments are typically transported out of the dermis by macrophages or diffusion into streams of blood and are distributed in the patient's body.

Tattoo pigments, however, cover a range of colors, including black, white, blue, red, green, and others. Dark blue-black amateur and professional tattoos usually contain amorphous carbon, graphite, India ink, and organo-metallic dyes. There has been, therefore, no single laser most suitable for tattoo removal by thermal photoablation.

Laser-based tattoo removal, therefore, has been accomplished using a variety of lasers to induce thermal photoablation, including, but not limited to: Q-switched Nd:Yag lasers typically operating at 1064 nanometer (1 nanometer=1 nm=$1\times10^{-9}$ m) or 532 nm, with 5-20 nanoseconds (1 nanosecond=1 nsec=$1\times10^{-9}$ sec) pulse duration; Q-switched Alexandrite lasers typically operating at 755 nm, with 100 nsec pulse duration; and Q-switched Ruby lasers typically operating at 694 nm, with 20-40 nsec pulse duration.

These lasers are collectively known as nsec-type lasers. Typically, a cream to numb the skin is applied to the patient prior to the treatment to reduce the level of pain felt during the treatment. Pulses of the laser light, typically of the order of 5 to 100 nsec, are then directed through the surface of the subject's skin and are absorbed by the tattoo pigment. The light breaks the pigment into particles by thermal photoablation. The particles are small enough to be absorbed by the body.

The principal sources of trauma in the nsec laser removal of tattoos are the heating of the skin, which causes damage similar to a second-degree burn, and the formation of highly localized shock waves in the dermis that cause undesirable tissue damage. Even with the use of numbing agents, the patient normally experiences pain during the treatments. After each treatment, the body's scavenger cells remove the particles of pigment from the treated pigmented areas. The skin and tissue damage then heals over the next several weeks, although healing time varies depending upon the size and depth of the tattoo, the procedure used and the patient's healing process. More than a dozen treatments, which can span over 1 year or more, may be necessary to complete the process. Some scarring or color variations are likely to remain.

These current laser procedures for tattoo removal are painful, expensive, rarely 100% effective, may leave permanent scarring, and typically require multiple treatments spread over a long period of time.

Because of the problems related to the prior art, improvements in tattoo and pigment removal systems and methods are needed that more completely remove tattoos, pigments, and blemishes, do not leave permanent scarring, do not cause burning, reduce or eliminate pain, and may be accomplished with fewer treatments spanning a shorter total time period.

SUMMARY OF THE INVENTION

Briefly described, the present invention provides methods and apparatus for tattoo, pigment, and blemish removal, and other dermatological treatments, preferably via multi-photon processing. The current invention preferably utilizes two laser beams, one to create a channel beginning at the top layer of the skin and ending in the vicinity of the pigment targeted for removal (the "Secondary Laser"), and another laser beam that passes through said channel and ablates said pigments (the "Main Laser"). These two beams can be directed to the patient's skin at approximately the same time, or where one is in advance of the other, depending on factors that include skin type, skin conditions, and pigment types.

The channel created by the Secondary Laser acts as a waveguide for the Main Laser toward the pigments, thus minimizing Main Laser pulse energy loss and allowing for a lower Main Laser entrance intensity. The channel also allows for ablated pigments and material to escape from the skin.

It is an object of the invention to provide improved techniques of removing tattoos, pigments, and blemishes from skin where burning of the skin, scarring of the skin, and pain are minimized through the use of a laser multi-photon processing.

It is another object of the invention to provide improved techniques of removing tattoos, pigments, and blemishes from skin where removal can be accomplished in fewer treatments over a shorter period of time than prior methods.

It is another object of the invention to provide improved techniques of removing tattoos, pigments, and blemishes from skin where the channel created by the Secondary Laser allows for the use of a lower intensity Main Laser.

It is another object of the invention to provide improved techniques of removing tattoos, pigments, and blemishes from skin where the ablated matter may escape from the skin via the channel that the Secondary Laser created.

It is another object of the invention to provide improved techniques of removing tattoos or pigments from skin where a laser of a single wavelength can remove said tattoos or pigments regardless of color.

DESCRIPTION OF THE PREFERRED EMBODIMENTS

The present invention relates to methods and apparatus for dermatological treatment that use multi-photon processing events as well as channel creation to reach material to be treated or removed. In particular, the present invention is directed to tattoo, pigment, and blemish removal using two lasers, a Secondary Laser, which creates a channel within the skin, and a Main Laser, which passes through said channel and removes pigments or material using multi photon ablation. These two beams may be directed to the patient's skin coaxially at approximately the same time, or where one is in advance of the other, depending on factors that include skin type, skin conditions, and pigment types.

The Secondary Laser

A purpose of the Secondary Laser is to create a channel that may begin at the outermost layer of skin and terminate in the area of the skin where material, such as tattoo ink or pigmented skin, is targeted for ablation. This Secondary Laser has a preferred pulse duration of 1 to 20 nsecs, although a range of 0.1 to 100 nsec may be used, and its pulse duration may be 1,000 to 100,000 longer than that of the Main Laser, and hence at a much lower power. While the preferred focal spot diameter for the Secondary Laser may be from 50 to 250 micrometers, its focal spot diameter must be large enough to create a channel so that the Main Laser may pass through the channel, preferably 2 to 3 times larger than the diameter of the Main Laser's focal spot. The preferred intensity of the Secondary Laser is in the range of $10^8$ to $10^9$ W/cm$^2$, although a range of $10^7$ to $10^{10}$ W/cm$^2$ may be used but may produce less optimal results. A laser beam with a 1064 nm wavelength may be used, although other wavelengths may also be used. Repetition rates of 5 to 100 Hz are preferred, although repetition rates up to a range of 1 kHz may be used but may have less optimal results. By way of example, an Nd/YAG laser system may play the role of the Secondary Laser.

The channel that the Secondary Laser creates may provide a waveguide for the Main Laser to reach the targeted material, whereby energy losses of the Main Laser's pulses are reduced and may be minimized. Thus, a lower energy Main Laser may be used in contrast to when no channel is created. Additionally, ablated material, such as ablated ink pigments, may escape the body via the channel.

The Main Laser

The Main Laser beam may enter the channel created by the Secondary Laser, reach the material to be ablated, and ablate the material. Preferably, the Main Laser will be a femtosecond laser with: a relatively low energy, for example in the range of 2 to 5 mJ/pulse; a pulse duration in the range of 50 to 100 fsec, although a range of 10 to 500 fsec is possible; a focal spot diameter in the range of 30 to 80 micrometers, although the diameter could be smaller or greater depending on the focal spot diameter of the Secondary Laser; and a preferred intensity in the range of $10^{13}$ to $10^{15}$ W/cm$^2$, although a range of $10^{12}$ to $10^{16}$ W/cm$^2$ may be used. The Main Laser beam's wavelength is preferably 800 nm, although it may have a different wavelength. Repetition rates of 5 to 100 Hz may be used, although repetition rates up to 1 kHz may also be used. By way of example a Ti/Sapphire laser system may play the role of the Main Laser.

In a preferred embodiment, the Main Laser's ultrashort and ultraintensive beam may initiate multi-photon processes, also called here multi-photon ablation, that may break down the targeted material, such as pigment inks, and associated molecular bonding without providing significant heat or local skin burning. Broken down pigments and molecules may escape the skin through the channel and/or by moving down to the flow of blood. Multiple treatments of the targeted treatment areas may therefore be completed in significantly shorter intervals compared to thermal laser-based tattoo removal treatments where burns caused by the laser treatment must be given time to heal between treatments.

In contrast to a thermal ablation process, which is typically generated by relatively low intensity but relatively high energy laser pulses that may initiate a single-type photon absorption process, multi-photon processing or ablation, utilizes a very high-intensity laser pulse, i.e., many photons in a small volume at the same time, where the density of photons is so great that during an absorption event many photons are absorbed simultaneously, which means that these many photons are absorbed by a particle, such as a molecule, atom, or ion, in a time period that is shorter than the relaxation time of the given particle.

Multi-photon processing also differs from thermal photoablation in that the low amount of energy per pulse involved in multi-photon processing allows the ablation to be very localized, very fast and result in no or negligible thermal heating or shocking of any surrounding material. For instance, by focusing a 2 mJ pulse of laser light that has a temporal pulse length in the range from 100 to 300 femtoseconds in duration—although the pulse duration could be shorter, for example 10 fsec, or longer, for example 500 fsec—to a small enough focal spot so the intensity is equal to or greater than $10^{12}$ Watts/cm$^2$, a multi-photon processing event may be initiated. This may result the pigment materials being broken into very small particles and in the dissociation of molecules. Such pulses may be obtained from, for instance, a suitably configured Titanium doped Sapphire (Ti:Sapphire) solid state laser.

The number of photons absorbed simultaneously by the particles in multi-photon ablation may be in the range of 5 to 10 photons per particle on the low end, and 100 photons or more per particle on the high end. The density of photons in a pulse is so high that the number of photons absorbed simultaneously is very large; hence multi-photon ablation may occur even where the energy of the pulse is low, in the range of 2 to 5 mJ or less. This amount of energy is sufficiently low that little or no damaging thermal heating of the surrounding tissue occurs as the energy diffuses. This is in marked contrast to thermal ablation with low-intensity pulsed lasers where only a single photon is absorbed in any given absorption event, and the pulse energy necessary for photoablation is so high that damaging heating of the surrounding tissue occurs as the heat diffuses.

"Few photon processes", for example, processes that involve not more than 2 to 3 photons in a single absorption event, also tend to result in thermal ablation, even though few-photon processes are sometimes inaccurately labeled "multi-photon processes" in some literature.

For a multi-photon process to be useful for treating skin discolorations and tattoos, the intensities of the laser pulses have to be very high. One way to simultaneously achieve both the high intensity and low energy is by using ultra-short laser pulses. In laser physics, ultra-short pulses are typically defined to be pulses up to 10 psec in duration, but preferably 50 to 100 fsec or even shorter. Moreover, the multi-photon ablation process is practically independent of the pigment color as the process does not depend on differential absorption by the pigment. Using multi-photon processing to remove pigment from the skin does not, therefore, require using different laser wavelengths for different pigments. This is in sharp contrast to thermal photo-ablation processes where the wavelength has to be chosen carefully to maximize the interaction with the specific pigment, or pigments, used in the tattoo, while allowing for sufficient dermal penetration to reach the pigment and at the same time avoiding absorption in the natural skin pigment, the melanin.

In the present invention, the channel in the skin, created by the low intensity Secondary Laser beam and that leads towards the pigment, or tattoo ink, may allow the very high intensity Main Laser to be rapidly delivered to the pigment.

When the two laser wavelengths used in the present invention are in the infra-red, they can penetrate deep into the dermis. The necessary high intensities on the target material may therefore be accomplished by using, for instance, a short focal length lens to focus the laser beams directly on the pigment, while the Secondary Laser low intensity laser beam may be focused with a longer focal length to create an elongated channel in the skin directly to the location of the pigments. By adjusting the Main Laser beam intensity by altering the focal spot on the pigments, the intensity within the focal volume can exceed the threshold intensity necessary to initiate multi-photon processing.

Preferred embodiments of the invention will now be described in detail by reference to the accompanying drawings in which, as far as possible, like elements are designated by like words and numbers.

Although every reasonable attempt is made in the accompanying drawings to represent the various elements of the embodiments in relative scale, it is not always possible to do so with the limitations of two-dimensional paper. Accordingly, in order to properly represent the relationships of various features among each other in the depicted embodiments and to properly demonstrate the invention in a reasonably simplified fashion, it is necessary at times to deviate from absolute scale in the attached drawings. However, one of ordinary skill in the art would fully appreciate and acknowledge any such scale deviations as not limiting the enablement of the disclosed embodiments.

There are at least two preferred embodiments of the invention. One embodiment provides an optical device for the Main Laser beams and Secondary Laser beams with the same wavelength, for example, Ti/Sapphire laser with wavelength of 800 nm (1 nm=$10^{-9}$ m), which compressed (fsec) and uncompressed (sub-nsec) beams have the same wavelength of 800 nm. In such a configuration, both beams are directed to an optical system, their expenders and two spherical lenses. One lens, the role of which may be to focus nsec- or sub-nsec-type pulses of the Secondary Laser beam, may have a hole in its center. The hole may be sufficient in diameter to allow the Main Laser Beam to propagate through the lens's hole without obstruction and to be focused at the same skin spot where the Secondary Laser beam is focused. In some cases, when it is necessary to create a longer channel in the skin toward a pigment, for instance where a "professional" tattoo must be reached, then the spherical lens with hole may be replaced by a conical lens (so called "axicon") which also have a hole in its center to allow propagation of the Main Laser beam pulses to occur without obstruction.

The second embodiment provides an optical device where the Main Laser beams and the Secondary Laser beams are of two different wavelengths. The preferable optical device may consists of two spherical lenses without holes, one said lens for focusing the Secondary Laser beam and the second lens for focusing the Main Laser beam. The Secondary Laser beam may be well reflected by interferometric mirror, whereas the Main Laser beam, with a significantly different wavelength, may pass through the mirror with only minimal absorption of its energy. As in the first embodiment, the lens for focusing the Secondary Laser beam pulse may be replaced by an axicon in order to create a longer channel in the skin toward a pigment of the tattoo.

By using a relatively high-repetition rate femtosecond laser, and repeating the localized, multi-photon process event initialization along the location of the pigment, that may, for instance, be a tattoo, the entire tattoo may be removed with little or no damage to the surrounding tissue. This process may be accomplished manually, or under the guidance of a computer, or through a combination thereof.

These and other features of the invention will be more fully understood by references to the following drawings.

Figure 1:
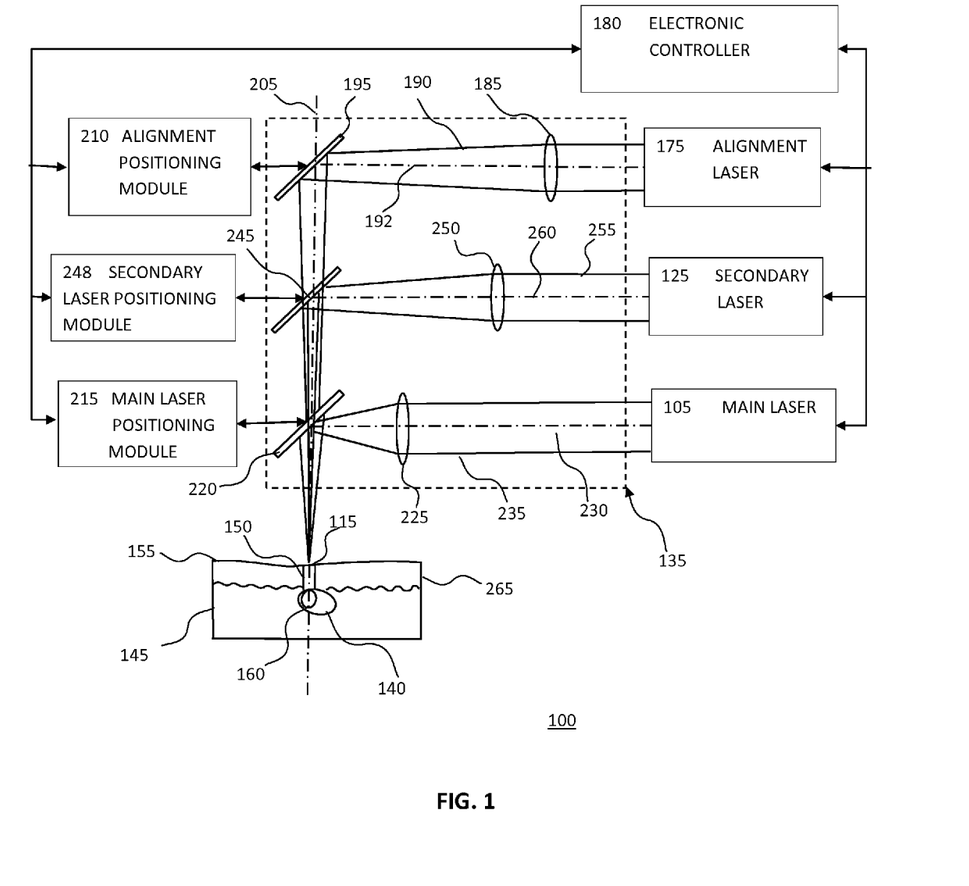
FIG. 1 shows a schematic overview of a system and method of removing a tattoo using a two laser protocol of the present invention.

FIG. 1 shows a schematic overview of a system and method of removing a tattoo using a two laser protocol of the present invention.

A secondary pulsed laser 125 may be used to create a temporary channel 150 by ablation. The temporary channel 150 may lead from the surface of the skin 155 of a patient to a granule of tattoo pigment 140 lying within the dermal layer 145.

An ultra-short pulse main laser 105 may then be used to initiate a multi-photon process 160 in a vicinity of a granule of tattoo pigment 140. The multi-photon process 160 may then breakup the granule of tattoo pigment 140 into fragments that may exit the patient's skin via the temporary channel 150 as a gas or liquid vapor. Breaking up the granule of tattoo pigment 140 may also disrupt a light reflecting property of the pigment, so that the fragments of the pigment may no longer visible to human eyes.

FIG. 1 also shows an optional alignment laser 175 that may, for instance, be a He—Ne continuous laser having an operational wavelength in the visible region of the spectrum at 632.8 nm as well as an optical system 135 for aligning the lasers.

The lasers and their alignment may, for instance, be controlled by an electronic controller 180 that may include one or more suitably programmed electronic controllers. The electronic controller 180 may, for instance, control a main laser positioning module 215, a secondary laser positioning module 248 and an alignment positioning module 210.

The main laser positioning module 215 may, in turn, control a main-laser beam-combiner 220 and a main-laser focusing-element 225 that together may bring a main-laser optical axis 230 into alignment with a common optical axis 205, and focus the main-laser beam 235 to a focal spot 115 that may be on the surface of the skin 155 or may be on the granule of tattoo pigment 140.

Similarly, the secondary laser positioning module 248 may, in turn, control a secondary-laser beam-combiner 245 and a secondary-laser focusing-element 250 that together may bring a secondary-laser optical axis 260 into alignment with the common optical axis 205 and focus the secondary-laser beam 255 to a focal spot 115 that may lie on the surface of the skin 155 and may be coincident with the focal spot of the main laser.

The optional alignment positioning module 210 may control an optional alignment mirror 195 and an optional alignment focusing element 185 that may together focus the alignment laser beam 190 to a focal spot 115 that may be on the surface of the skin 155 of the patient, and may bring the optional alignment laser optical axis 192 into alignment with the common optical axis 205.

One of ordinary skill in the art will, however, appreciate that the femtosecond pulses from the ultra-short pulse main laser 105 may be delivered to the area of interest on the patient via a delivery optic such as illustrated in FIG. 1 and/or by a fiber optic or some combination thereof. The fiber optic may, for instance, also deliver the main-laser beam 235 through the channels created by the secondary-laser beam 255.

Figure 2:
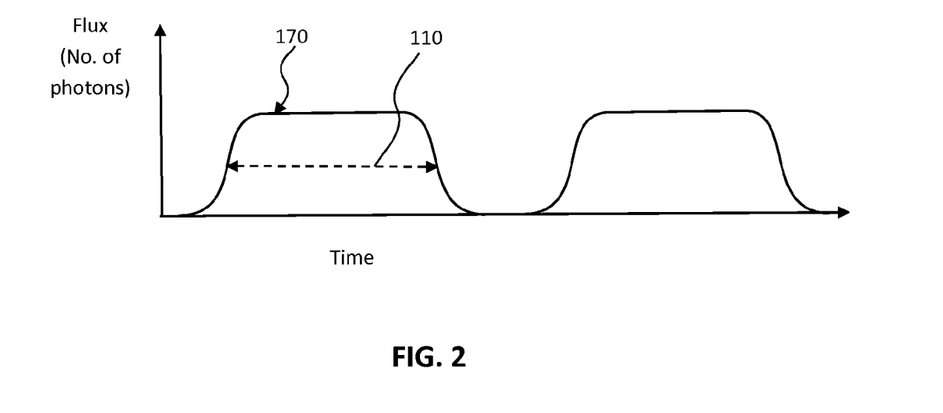
FIG. 2 shows a schematic view of a laser pulse.

FIG. 2 shows a schematic view of a laser pulse in a graph with the flux, or number of photons per unit time, plotted against time. The pulses 170 have an energy, measured in Joules, that is proportional to the total number of photons in the pulse and may be represented by the area under the pulse outline. The pulse has a pulse length 110 that is typically taken as the full width of the pulse at half maximum intensity. Pulse length is measured in seconds. The power of a pulse is the energy per unit time and is given by the energy divided by the pulse length and is measured in Joules/second, or Watts. The intensity of the pulse is given by the power per unit area of the beam and is typically greatest at the focal spot and is given by the power divided by the area of the focal spot and is measured in Watts/m$^2$, or as W/cm$^2$.

Figure 3:
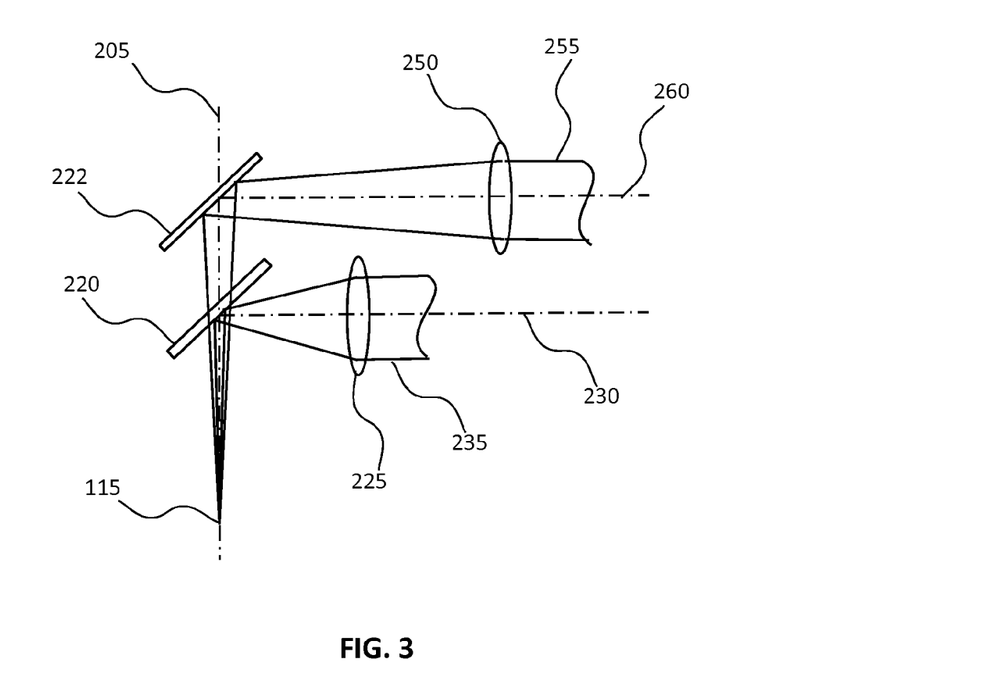
FIG. 3 shows a schematic view of an optical system of a preferred embodiment of the present invention.

FIG. 3 is a schematic drawing of an exemplary device of the present invention for providing a channel in the skin with nsec-type laser pulses from a secondary-laser beam 255, while the channel enables fast access for ultrashort and very high intensity laser pulses for multi-photon treatments, including the removal of pigments and tattoo inks, from a main-laser beam 235. The multi-photon processing treatment device includes a very high intensity femtosecond laser and associated delivery optics for it.

The delivery optics may, for instance, include a secondary-laser mirror 222 and a main-laser beam-combiner 220 which together may align a secondary-laser optical axis 260 and a main-laser optical axis 230 along a common optical axis 205. The delivery optics may also include a secondary-laser focusing-element 250 that may focus the secondary-laser beam 255 to a focal spot 115, and a main-laser focusing-element 225 that may focus the main-laser beam 235 to a focal spot 115 that may be coincident with the focal spot formed by the secondary-laser beam 255.

The femtosecond main-laser beam 235 may, for instance, be from a suitably configured Titanium doped sapphire (Ti:Sapphire) solid state laser as supplied by, for instance, COHERENT Inc, of Santa Clara, Calif. Such a laser may be operating at near infra-red wavelengths centered at 800 nm and emitting femtosecond pulses having pulses with a temporal duration in the range of 50 fsec and 100 fsec, a pulse energy of 0.5-5 mJ per pulse and a repetition rate of 10 Hz-100 Hz, and up to 1 kHz with up to 3 mJ pulse energy.

The femtosecond main-laser beam 235 may instead be from a suitably configured laser made using Cr doped Forsterite, or Er- and Yb-doped fibers, or some combination thereof.

The femtosecond pulses may be delivered to the area of interest on the patient via a delivery optic and/or a fiber optic through the channels created by the Secondary Laser beam pulses, for example nsec- or sub-nsec-type laser beams. FIG. 3 shows delivery optics for both the secondary-laser beam 255 and the main-laser beam 235. The ultrashort and nsec-type laser beams may be of different wavelengths, for example, the nsec-type secondary-laser beam 255 may have a wavelength of 1064 nm and ultrashort main-laser beam 235 may have a wavelength of 800 nm. The nsec-type secondary-laser beam 255, that may for example, have 10 nsec pulses, may be focused by secondary-laser focusing-element 250, may be redirected by full intensity reflecting secondary-laser mirror 222 and may pass through secondary-laser mirror 222, which may be an interferometric mirror, and which may be almost transparent for the wavelength 1064 nm. The Main Laser beam 235 may be focused by main-laser focusing-element 225, may be redirected by main-laser beam-combiner 220 which may be an interferometric mirror acting as reflecting mirror at 800 nm, and which may almost fully reflect the Main Laser beam 235 having wavelength of 800 nm. After passing main-laser beam-combiner 220 both beams may travel coaxially along a common optical axis 205 and may be focused below the skin surface into the material targeted for treatment, for instance an area containing pigments. The diameter of the Secondary Laser beam may larger than the Main Laser beam, so said Main Laser beam may travel toward the targeted area, for instance tattoo inks, through the channel created by said Secondary Laser beam with little or no absorption.

Figure 4:
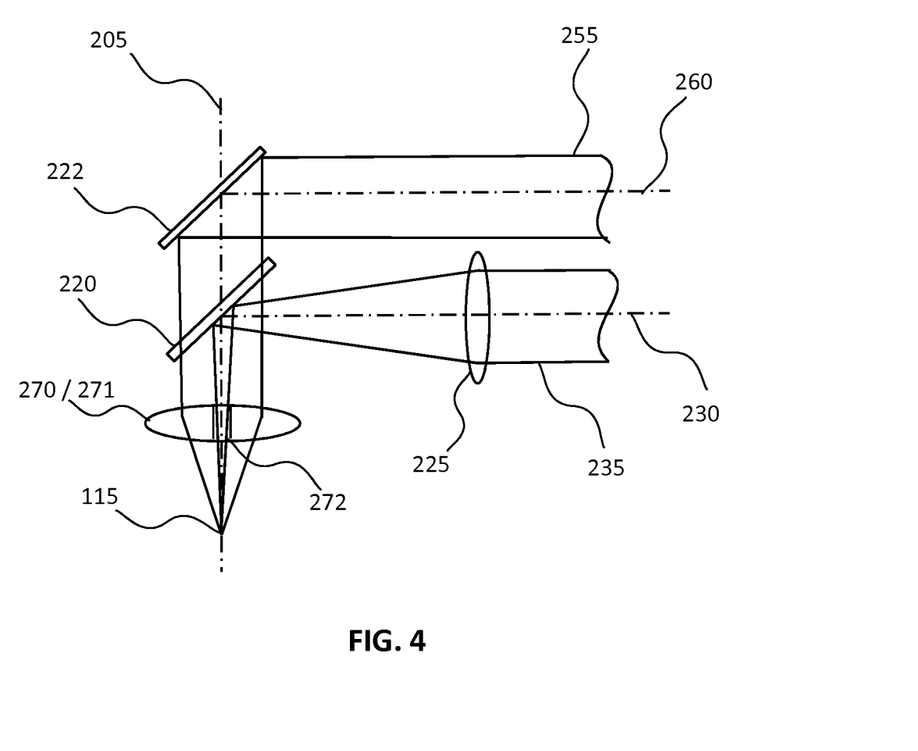
FIG. 4 shows a schematic view of an optical system of a further preferred embodiment of the present invention.
Figure 5:
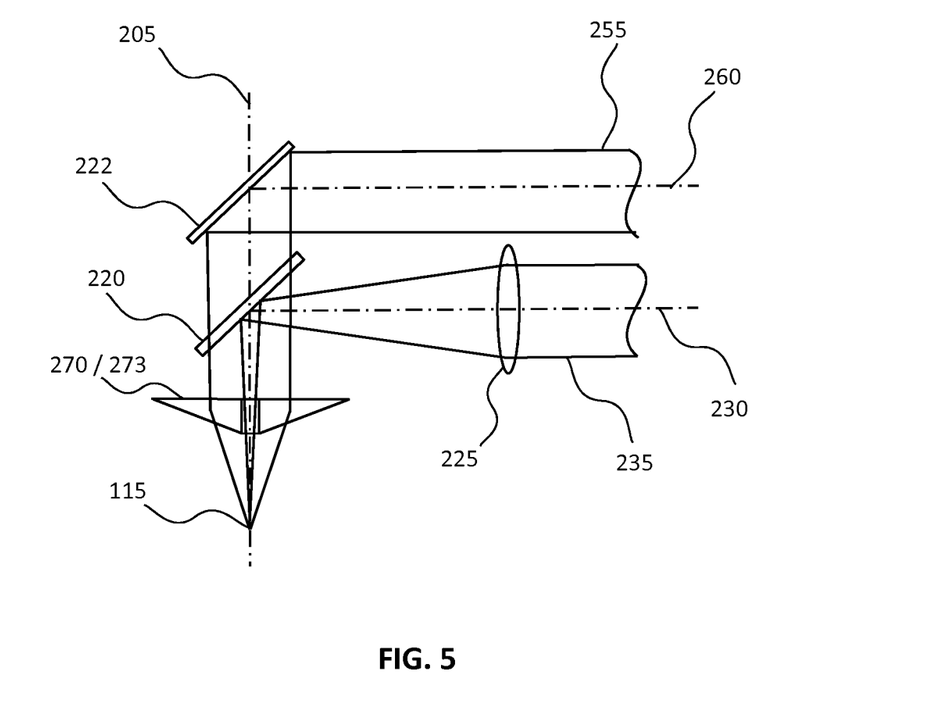
FIG. 5 shows a schematic view of an optical system of yet another preferred embodiment of the present invention.

When both beams have the same wavelength, the optical scheme in FIG. 3 may be modified as illustrated in FIG. 4 and FIG. 5. The main difference between FIG. 4 and FIG. 5 is in the use of an optical scheme having the focusing element with a through-hole 270 be an Axicon 273, or conical lens, with a hole in its center instead of a lens 271 made of spherical surfaces and also with hole in its center. In both optical schemes of FIGS. 4 and 5 the secondary-laser beam 255 may first be reflected by secondary-laser mirror 222 that may be angled at approximately 45 degrees with respect to the secondary-laser optical axis 260. The secondary-laser beam 255 may then pass through the Beam Splitter, or main-laser beam-combiner 220, and may then be focused by a focusing element with a through-hole 270. The focusing element with a through-hole 270 may, as shown in FIG. 4, be a lens 271 made of spherical surfaces, or, as shown in FIG. 5, an Axicon 273, or conical lens.

In both optical schemes the main-laser beam 235 may first be focused by main-laser focusing-element 225 and may then travel through the through-hole in focusing element 270. As stated above, the focusing element with a through-hole 270 may be a lens 271 made of spherical surfaces as shown in FIG. 4, or it may be an Axicon 273, or conical lens as shown in FIG. 5.

As in the arrangement of FIG. 3, after passing through the focusing element with a through-hole 270 both beams may be travelling coaxially along a common optical axis 205 and may be focused to a common focal spot 115 that may be located below the skin surface in the targeted area, that may, for instance, be an area containing pigments. The focal diameter of the Secondary Laser Beam may be larger than the focal diameter of the Main Laser beam, so the Main Laser beam can travel toward the targeted area through the channel created by the Secondary Laser beam practically without absorption. In the case when a significantly elongated and uniform channel in the skin is required, the Axicon 273, or conical lens, of FIG. 5 may be used for focusing the Secondary Laser beam instead of the lens 271 made of spherical surfaces as shown in FIG. 4.

Figure 6:
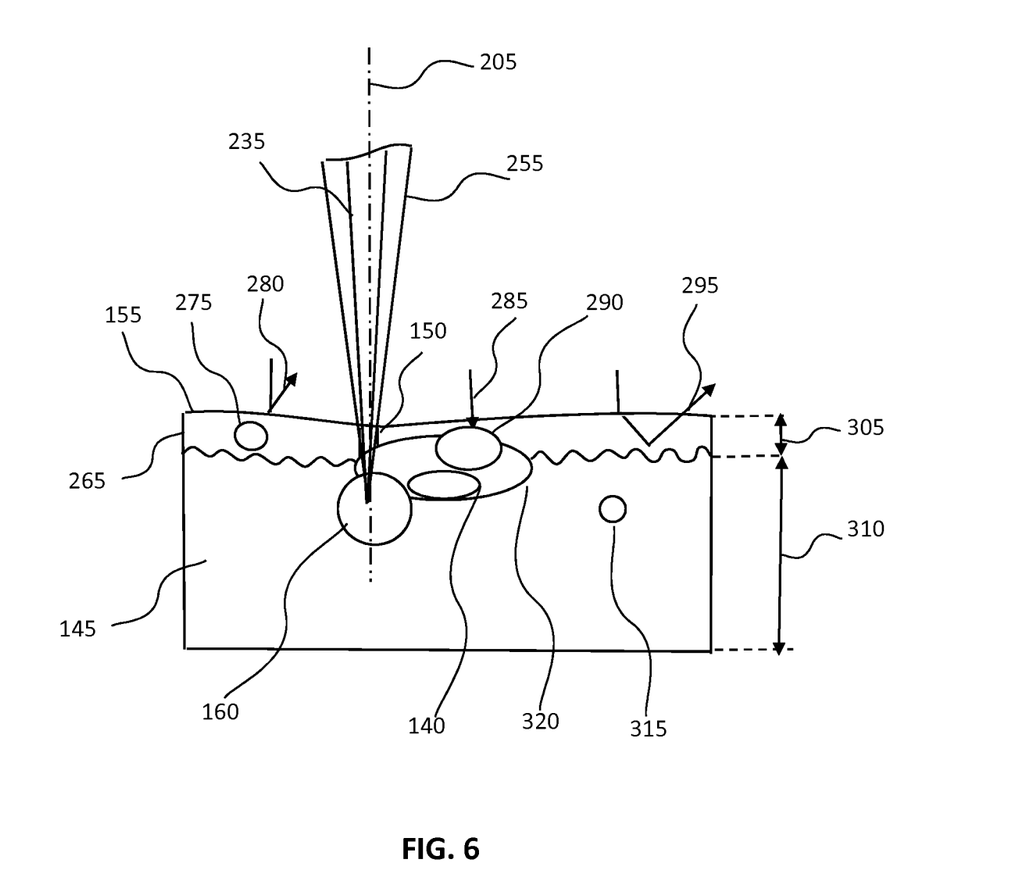
FIG. 6 shows a close up schematic cross-sectional view of two laser tattoo removal in accordance with the present invention.

FIG. 6 schematically illustrates the creation of a channel 150 in human skin from its surface 155 to the targeted area. Channels 150 may be created using the secondary-laser beam 255, and may allow for fast access of the main-laser beam 235, which may include ultrashort and very high intensity laser pulses into the area of interest, for breaking pigments 320 into small particles and breaking bonds of large molecules. The channel created by the Secondary Laser beam with the Main Laser beam concentrically located inside the channel and reaching the area for multi-photon interaction with tattoo inks is illustrated.

The tattoo may, for instance, be made up of one or more granules of tattoo pigment 140, that may include a variety of tattoo inks such as, but not limited to, black tattoo ink 320, blue tattoo ink 290, red ink, green ink, or some combination thereof.

The tattoo may be located within the dermal layer 145 that lies immediately beneath the epidermis 265 and the surface of the skin 155. The epidermis thickness 305 in regions of normal placement of tattoos, i.e., arms, legs, back, face, torso, is typically about 100 μm. The dermal thickness 310 in these regions is typically about 4 mm.

The epidermis 265 may contain naturally occurring pigments such as, but not limited to, melanin 275 that absorbs incident light. The dermal layer 145 may contain other vessels such as, but not limited to, hemoglobin 315.

Light may interact with the skin in a number of ways such as, but not limited to, reflectance 280 off the dermal surface 155, absorption 285 by the epidermis 265, and dermal and epidermal remittance 295.

In order to minimize the skin's light attenuating mechanisms such as, but not limited to, those listed above, the method of the present invention may use a secondary-laser beam 255 to create a temporary channel 150. This temporary channel 150 may then be used to allow and to guide propagation of a main-laser beam 235 to a vicinity of the granule of tattoo pigment 140, where the main-laser beam 235 may be focused to an intensity sufficient to initiate a multi-photon process 160, as described in detail above. The multi-photon process 160 may break up the granule of tattoo pigment 140, including any black tattoo ink 320 or blue tattoo ink 290 particles that may be sufficiently close, as also described above.

The fragments of pigment and pigment molecules may escape via the temporary channel 150 into the atmosphere, or they may also, or instead, diffuse down through the dermal layer to blood vessels located beneath.

The tattoo removal process may include repeating breaking the granules of tattoo pigment until the remnants of the granules of tattoo pigments leave no visible sign of a tattoo. One measure of the tattoo being removed may be that any tattoo pigments that may remain, produce substantially no reflection of visible light observable by a human observer having 20/20 vision at light levels of 750-1000 lux.

Figure 7:
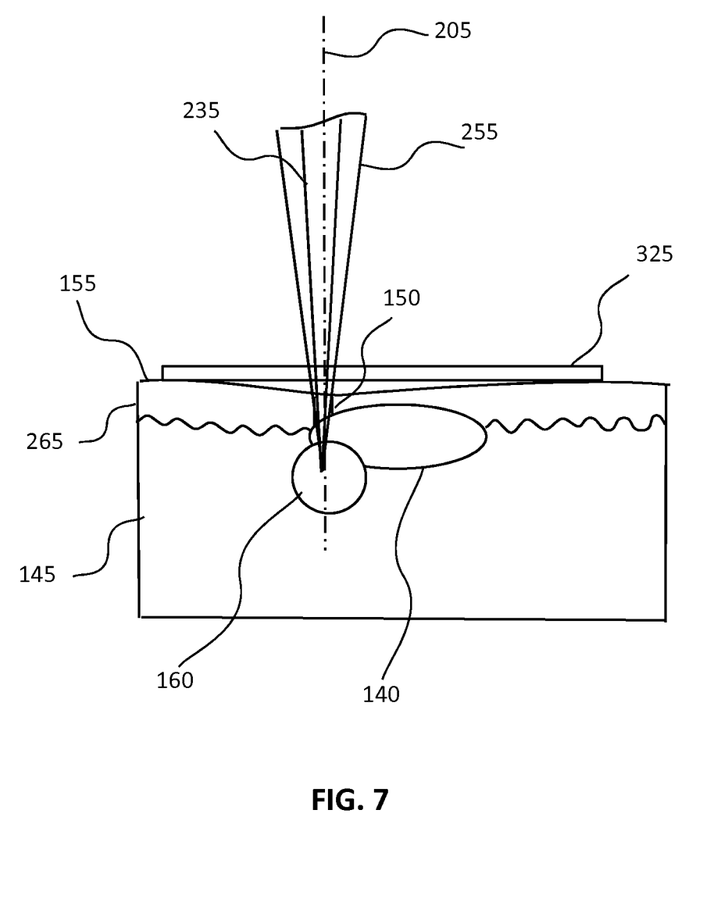
FIG. 7 shows a close up schematic cross-sectional view of two laser tattoo removal in accordance with a further embodiment of the present invention.

FIG. 7 shows a close up schematic cross-sectional view of two laser tattoo removal in accordance with a further embodiment of the present invention in which a second-laser beam 235 may be focused through a temporary channel 150 that may have been created by a first-laser beam 255. The temporary channel 150 may extend from the surface of the skin 155 through the epidermis 265 to a granule of tattoo pigment 140, typically located near an upper region of the dermal layer 145.

The focused second-laser beam 235 may be sufficiently intense to initiate a multi-photon process 160 that may break up the granule of tattoo pigment 140.

The surface of the skin 155 in a region including the temporary channel 150 may be covered by a layer of water-impermeable material 325 that may be substantially transparent to both the first-laser beam 255 and the second-laser beam 235.

The layer of water-impermeable material 325 may reduce any loss of moisture from the skin during the creation of the temporary channel 150 or during the multi-photon process 160 breakup of the granule of tattoo pigment 140.

The layer of water-impermeable material 325 may be any suitable material such as, but not limited to, a mm or thinner layer of mica, a polymer coated onto the skin surface, a gel, a thin glass or plastic plate, or some combination thereof. In a further preferred embodiment of the invention, the layer of water-impermeable material 325 may be a sheet of mica having a thickness of 100 μm or less.

Examples of Use of the Invention

In a first test, Example 1, two laser beams with very different pulse durations, whereas approximately 100 fsec of very high intensity laser pulses, for example an intensity on pigments or inks inside the skin of more than $10^{12}$ W/cm$^2$, were applied for multi-photon processing via the main laser, and approximately 10 nsec low intensity pulses from the secondary laser created elongated channels in the skin. The main laser was Ti/Sapphire laser with a wavelength of 800 nm and the secondary laser was a 10 nsec Nd/YAG laser with a 1064 nm wavelength. Both lasers were run at a 10 Hz repetition rate. Because of the significant difference in the wavelengths, the optical scheme of FIG. 3 was applied. The 100 fsec laser pulses were directed to tattoo inks via channels created in the skin by 10 nsec pulses. The pulses of both lasers were synchronized. The 100 fsec pulses were reaching tattoo inks practically without absorption while traveling to the inks and were breaking the inks into small particles and large molecules to small ones by a multi-photon process. The shattered remnants were leaving the tattoo ink areas to outside the skin through the channels and diffusing inside the skin into blood streams. This test of the invention demonstrated removal of a 7-color tattoo from a small testing area of about 1 cm$^2$ in just several sessions without scarring.

Additional testing was performed using lasers with 100 Hz and 1 kHz repetition rates, but with about 10-20 times significantly lower energies per pulse for each laser. Results for tattoo removal were similar to those presented above, although the rate of removal tattoo was not proportional to repetition rates of the lasers.

In a second test, Example 2, two laser beams with the same wavelength were used. Both the optical schemes shown in FIGS. 4 and 5 were tested. As in Example 1, the two laser beams had very different pulse durations. The tests demonstrated the removal of multi-color tattoos. The optical scheme of FIG. 5 provided similar results to those using the optical scheme of FIG. 4, but did not require moving the lens 271 made of spherical surfaces along the axis of the secondary laser beam to create sufficiently long channels in the skin. Of course, movement of lens 271 along the axis of the secondary laser beam, which is the common axis for both laser beams, did not affect the main laser beam, which was traveling inside the hole in the lens without interacting with said lens. Similarly, as in Example 1 that employed the optical scheme shown in FIG. 3 above, the Main Laser's approximately 100 fsec ultrashort and very high intensity laser pulses of $10^{12}$ W/cm$^2$ or greater on the pigment or inks were applied for multi-photon processing. The 100 fsec laser main laser was Ti/Sapphire with a wavelength of 800 nm. For convenience, the secondary laser beam's nsec-type pulses also had a wavelength of 800 nm. This was the result of the second beam being obtained by splitting an 800 nm laser beam before the compressor, where the pluses are about 0.2 ns in temporal duration. This beam was focused with the lens 271 made of spherical surfaces and which had a centered through-hole. The second part of the beam was compressed down to ~100 fsec and then focused by the main-laser focusing-element 225. The focusing main-laser beam was propagated through the hole in the focusing element with a through-hole 270 that in the optical arrangement of FIG. 4 was a lens 271 made of spherical surfaces, and in the optical arrangement of FIG. 5, an Axicon 273, or conical lens. The main-laser beam 235 was focused in to the channel created by the secondary-laser beam 255, directly onto the skin pigments or tattoo inks, which were disintegrated by means of multi-photon processes. In both cases, the Ti/Sapphire laser used to generate both the main-laser beam 235 and the secondary-laser beam 255 was running at a repetition rate of 5 Hz with a minimum energy for each beam of about 10 mJ/per beam per pulse and up to 30 mJ/per beam per pulse.

Creation of white spots on the surface of the skin has been observed as a result of applying the Secondary and Main Lasers. Focusing the Secondary and Main Laser beams through glass or mica before said beams reach the skin decreased the intensity of the white spots. Glass was typically 150-200 µm thick and mica was as thin as 50 µm, although other thicknesses could be used. Both glass and mica have very good transparency for the Main Laser beam, operating at the wavelength of 800 nm and the Secondary Laser beam operating at the wavelength of 1,064 nm. However neither regular glass nor mica are transparent for deep UV radiation, hence protecting skin from burning by UV radiation from plasma created on surface of skin by Main Laser beam pulses.

Clinical Use

A clinical use of the multi-photon processing systems of present invention can be similar to this as presented in U.S. Pat. No. 8,187,256, which is incorporated herein, but slightly more complicated due to use of two laser beams instead one beam. In a preliminary examination, a tattoo may first be evaluated in terms of the relevant variables, which include the extent of the affected region, the depth of the ink layers, and the types of inks used in the tattoo. Other factors, such as the natural skin color surrounding the tattoo, the age of the patient, the quality of natural wound healing, and other factors including the patient's general health may be noted. A map of the tattoo may then be created, for example, from a white light image of the tattoo obtained by, for instance, a camera, that may be a CCD camera, and the imaging telescope operating under the control of a computer. Using image processing techniques, details of the physical location of the tattoo pigments may be obtained, including the depth of the pigmented layers. However, in contrast to using only a single ultrashort and very high intensity laser beam, by using the additional Secondary Laser beam for creating the channel in the skin, a patient-specific procedure for the tattoo removal could be less sensitive to the above-mentioned patient conditions.

In a manual treatment, the operator may choose the laser parameters such as, but not limited to, the power per shot, the number of shots, the repetition rate, the positioning, and the focusing requirements of the laser beam. The operator may then apply the ultrashort ultra very intense laser pulses to the area of interest being treated by multi-photon processes using a delivery optical system. Progress may be monitored by, for example, direct visual inspection, or by the use of a camera that may connected to a viewing monitor by means of a computer.

In a computer-controlled treatment, the delivery optical system can direct the Secondary Laser beams and the Main Laser beams to the area by, for example, an optics positioning system that may be part of the positioning unit. The operator may monitor progress by, for example, direct visual inspection, or by the use of a camera that may be connected to the viewing monitor. The camera may also be used in all treatments, manual or computer-controlled, to obtain and store still or video images and to record the progress of the removal procedure.

The treated area may be evaluated after one round of laser ablation. A further treatment may be advised, either immediately following the first treatment, or after one or more days. Based on experiments described above, it is expected that most individuals may only need just a few treatments in period of a several weeks but said period could be as short as one or two weeks.

Testing of this invention has shown practically total removal of a so called "professional tattoo" (which are different to "amateur tattoo" in that the ink is typically placed at a more shallow location beneath the skin than in professional tattoos) of 7 colors from small testing area without any significant pain, skin damage, or post-treatment scars.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention. Modifications may readily be devised by those ordinarily skilled in the art without departing from the spirit or scope of the present invention.

What is claimed:

1. A method of removing pigment from beneath the surface of the skin, comprising:
    creating a temporary channel from said surface of the skin to a vicinity of said pigment by ablating material using a first laser beam emanating from a laser, said first laser beam having a pulse length in a range from 0.1 nsec to 100 nsec and, being focused to have an intensity in a range of $10^7$ to $10^{10}$ W/cm² within a focal regions;
    directing through said temporary channel to said vicinity of said pigment, a second laser beam emanating from said laser or from a second laser, said second laser beam having a pulse length of 400 fsec or less and being focused to have an intensity of at least $10^{12}$ W/cm² in a focal region, thereby initiating a multi-photon ablation process in said vicinity of said pigment, and breaking said pigment into two or more constituent parts.

2. The method of claim 1 wherein an optical system is used to align said focal region of said first laser beam, when focused to have an intensity in a range of $10^7$ to $10^{10}$ W/cm², and said focal region of said second laser beam emanating from said laser or said second laser when focused to have an intensity of at least $10^{12}$ W/cm², to substantially coincide.

3. The method of claim 1 wherein said pigment comprises tattoo ink.

4. The method of claim 1 wherein when focused to have an intensity of at least $10^{12}$ W/cm², said beam emanating from said lasers have a pulse energy equal to or smaller than 10 mJ.

5. The method of claim 1 wherein said pigment is a granule of pigment of a tattoo; and further comprising repeating breaking said granules of pigment of said tattoo until said tattoo is substantially invisible.

6. The method of claim 1 further comprising a covering a patient's skin surface in a vicinity of said temporary channel with a layer of water-impermeable material that is substantially transparent to said first and second laser beams emanating from said one or two lasers.

7. The method of claim 6 wherein said water-impermeable material is a sheet of mica having a thickness of 300 μm or less.

* * * * *